United States Patent
Gatrell et al.

(10) Patent No.: US 12,295,854 B2
(45) Date of Patent: May 13, 2025

(54) ANNULAR CUTTING TOOLS FOR RESECTING A BONE GRAFT AND RELATED METHODS

(71) Applicant: DePuy Synthes Products, Inc., Raynham, MA (US)

(72) Inventors: Bernice Aboud Gatrell, Columbia City, IN (US); Rakshak Nemiraj, Bangalore (IN); Alexander D. Jones, Providence, RI (US); Thomas E. Wogoman, Warsaw, IN (US); Karthik Balasubramanian, Chennai (IN); Timothy Dolan, Goshen, IN (US)

(73) Assignee: Medos International Sarl, Le Locle (CH)

( * ) Notice: Subject to any disclaimer, the term of this patent is extended or adjusted under 35 U.S.C. 154(b) by 315 days.

(21) Appl. No.: 17/899,024

(22) Filed: Aug. 30, 2022

(65) Prior Publication Data
US 2022/0409384 A1     Dec. 29, 2022

Related U.S. Application Data

(62) Division of application No. 16/454,959, filed on Jun. 27, 2019, now Pat. No. 11,446,151.

(51) Int. Cl.
*A61B 17/16*     (2006.01)
*A61B 17/17*     (2006.01)
(Continued)

(52) U.S. Cl.
CPC ........ *A61F 2/4081* (2013.01); *A61B 17/1615* (2013.01); *A61B 17/17* (2013.01); *A61B 17/15* (2013.01); *A61B 2017/320024* (2013.01)

(58) Field of Classification Search
CPC .................................................. A61B 17/1637
See application file for complete search history.

(56) References Cited

U.S. PATENT DOCUMENTS 2,794,469 A  *  6/1957  Shortell  ............. B23B 51/0426
                                                    408/208
2,804,895 A  *  9/1957  Clement  ............. B23B 51/0426
                                                    144/1.1

(Continued)

OTHER PUBLICATIONS

[No Author Listed] BIO-RSA Angled Surgical Technique (product brochure), Tornier SAS, 2015, 16 pages.

(Continued)

*Primary Examiner* — Zade Coley
(74) *Attorney, Agent, or Firm* — Barnes & Thornburg LLP

(57) ABSTRACT

An annular cutting tool and related methods are provided for herein that exhibit improved durability, cutting performance, and/or reduced heat generation for bone graft resections. The annular cutting tool can include an annular body having cutting teeth with a flat, flared distal tip for greater durability. An extended gullet can be disposed between groups of adjacent cutting teeth to improve removal of bone debris away from the cutting teeth more and thus prevent binding during use. The annular cutting body can have a recessed surface portion to reduce the area of direct contact to bone and thus reduce heat generated. The recessed surface portion can also provide an area in which bone debris can accumulate away from the cutting teeth to prevent or reduce binding of the tool during use. The annular cutting body can also include a drill bit for drilling a hole in a resected bone graft.

20 Claims, 10 Drawing Sheets

(51) Int. Cl.
*A61F 2/40* (2006.01)
*A61B 17/15* (2006.01)
*A61B 17/32* (2006.01)

(56) References Cited

U.S. PATENT DOCUMENTS

| | | | | |
|---|---|---|---|---|
| 3,559,513 | A * | 2/1971 | Hougen | B23B 51/0473 |
| | | | | 408/56 |
| 3,605,527 | A * | 9/1971 | Gambale | A61B 17/1666 |
| | | | | 76/115 |
| 3,609,056 | A * | 9/1971 | Hougen | B23B 51/0426 |
| | | | | 408/206 |
| 4,586,857 | A | 5/1986 | Ohmi | |
| 5,171,111 | A * | 12/1992 | Kishimoto | B23B 51/0426 |
| | | | | 408/67 |
| 5,316,418 | A * | 5/1994 | Miyanaga | B23B 51/0426 |
| | | | | 408/209 |
| 5,632,747 | A * | 5/1997 | Scarborough | A61F 2/4644 |
| | | | | 606/86 R |
| 5,803,677 | A * | 9/1998 | Brutscher | B23B 51/0426 |
| | | | | 408/206 |
| 6,007,279 | A * | 12/1999 | Malone, Jr. | B23B 51/0426 |
| | | | | 408/206 |
| 6,089,867 | A * | 7/2000 | Filho | A61C 8/0006 |
| | | | | 433/175 |
| 6,250,856 | B1 * | 6/2001 | Miyanaga | B23B 51/0473 |
| | | | | 279/75 |
| 6,588,992 | B2 * | 7/2003 | Rudolph | B23B 51/0426 |
| | | | | 408/206 |
| 7,033,359 | B2 * | 4/2006 | Meller | A61B 10/025 |
| | | | | 606/80 |
| 7,553,313 | B2 | 6/2009 | Bagby | |
| 7,658,136 | B2 * | 2/2010 | Rompel | B23B 51/0426 |
| | | | | 83/835 |
| 8,070,755 | B2 * | 12/2011 | Maroney | A61B 90/06 |
| | | | | 606/102 |
| 8,162,967 | B1 | 4/2012 | Kaiser et al. | |
| 8,235,721 | B2 * | 8/2012 | Bagambisa | A61C 8/0089 |
| | | | | 433/201.1 |
| 8,366,713 | B2 * | 2/2013 | Long | A61B 17/1675 |
| | | | | 606/80 |
| 8,486,074 | B2 | 7/2013 | Steiner et al. | |
| 8,523,867 | B2 * | 9/2013 | Rauscher | A61B 17/1684 |
| | | | | 606/81 |
| 8,827,604 | B1 * | 9/2014 | Corey | B23B 51/0453 |
| | | | | 408/239 R |
| 8,876,825 | B2 * | 11/2014 | Victor | A61B 17/1668 |
| | | | | 606/80 |
| 9,814,587 | B2 * | 11/2017 | Goldberg | A61B 17/1659 |
| 11,446,151 | B2 | 9/2022 | Gatrell et al. | |
| 2003/0078610 | A1 * | 4/2003 | Yedlowski | A61F 13/046 |
| | | | | 606/179 |
| 2004/0193168 | A1 * | 9/2004 | Long | A61B 17/1684 |
| | | | | 606/80 |
| 2004/0210229 | A1 * | 10/2004 | Meller | A61B 10/025 |
| | | | | 606/80 |
| 2006/0130629 | A1 * | 6/2006 | Rompel | B23B 51/0426 |
| | | | | 83/866 |
| 2007/0071564 | A1 * | 3/2007 | Omi | B23B 51/0426 |
| | | | | 408/204 |
| 2008/0019785 | A1 * | 1/2008 | Keightley | B23B 31/11 |
| | | | | 408/204 |
| 2010/0278601 | A1 * | 11/2010 | Beynon | B28D 1/041 |
| | | | | 408/1 R |
| 2013/0333541 | A1 | 12/2013 | Karlen et al. | |
| 2014/0350561 | A1 * | 11/2014 | Dacosta | A61B 17/1682 |
| | | | | 29/428 |
| 2017/0042687 | A1 | 2/2017 | Boileau et al. | |
| 2017/0120357 | A1 | 5/2017 | Trautner et al. | |
| 2017/0143351 | A1 * | 5/2017 | Devitre | A61C 8/0087 |
| 2020/0405495 | A1 | 12/2020 | Gatrell et al. | |

OTHER PUBLICATIONS

[No Author Listed] BIO-RSA Surgical Technique Bony Increased Offset—Reversed Shoulder Arthroplasty (product brochure), Tornier SAS, 20 pages (No Date Listed).

[No Author Listed] BIO-RSA Bony Increased Offset—Reversed Soulder Arthroplasty (product brochure), Wright, Feb. 12, 2016, 20 pages.

* cited by examiner

Section C-C

ANNULAR CUTTING TOOLS FOR RESECTING A BONE GRAFT AND RELATED METHODS

CROSS-REFERENCE TO RELATED APPLICATIONS

This application claims the benefit of and is a division of U.S. patent application Ser. No. 16/454,959, filed Jun. 27, 2019, which is hereby incorporated by reference in its entirety.

FIELD

The present disclosure relates generally to annular cutting tools, and more particularly to an annular cutting tool designed to resect a bone graft with improved durability, cutting performance, and/or reduced heat generation during use, as well as methods of resecting bone grafts using such annular cutting tools.

BACKGROUND

During the lifetime of a patient, it may be necessary to perform a total shoulder replacement procedure on the patient, for example, as a result of disease or trauma. In a total shoulder replacement procedure, a humeral prosthesis is used to replace the natural head of the patient's humerus. The humeral prosthesis typically includes an elongated post component that is implanted into the intramedullary canal of the patient's humerus and a hemispherically-shaped prosthetic head component that is secured to the post component. In such a total shoulder replacement procedure, the natural glenoid surface of the scapula is typically resurfaced or otherwise replaced with a glenoid component that provides a bearing surface upon which the prosthetic head component of the humeral prosthesis articulates.

However, in some cases the patient's natural shoulder, including its soft tissue, has degenerated to a severe degree of joint instability and pain. In many such cases, it can be necessary to change the mechanics of the shoulder. Reverse shoulder implants can be used to do so. As its name suggests, a reverse shoulder implant reverses the anatomy, or structure, of the healthy shoulder. In particular, a reverse shoulder implant is designed such that the prosthetic head (i.e., the "ball" in the ball-and-socket joint), known as a glenosphere component, among other names, is secured to the patient's scapula, with the corresponding concave bearing (i.e., the "socket" in the ball-and-socket joint), known as a humeral cup, among other names, being secured to the patient's humerus. Such a reverse configuration allows the patient's deltoid muscle, which is one of the larger and stronger shoulder muscles, to raise the arm.

To secure the glenosphere component to the patient's scapula, a baseplate, sometimes referred to as a metaglene component, can be implanted onto the glenoid of the patient's scapula. For example, as shown in FIGS. 1A and 1B, a shoulder joint implant can comprise a metaglene component 60 that includes a platform 62 having a post 64 extending outwardly from its distal surface 66. The post 64 can have a bore 68 formed about a central axis A-A of the metaglene component 60 and can be configured to engage a locking screw or other coupling element protruding from a distal surface of a glenosphere component (not shown). The bore 68 can extend through the entire length of the post 64. The post 64 of the metaglene component 60 can be designed to be implanted into a void formed in a glenoid surface 28. Bone screws 80 can be positioned in some or all of the screw holes or apertures 74 and driven into, or otherwise secured to, the bone tissue of a patient's scapula 30, thereby fixing the metaglene component 60 in place.

In some patients, the glenoid may be severely eroded to an extent that the metaglene component 60 cannot be properly implanted. In such situations, surgeons may attach the metaglene component 60 to a bone graft that fills in the eroded space in the glenoid. The bone graft can be resected from an allograft or a part of the patient's body, such as, for example, the head of the humerus or portion of the femur. As shown in FIGS. 2A and 2B, an exemplary bone graft 90 for attachment to a metaglene component 60 can be shaped to have a generally cylindrical body having a proximal end 92 and a distal end 94. The proximal end 92 can be reamed or otherwise shaped to facilitate attachment to the distal side of the metaglene component 60. For example, the reamed proximal end 92 of the bone graft 90 can have a generally concave-shaped surface that mates with a generally convex-shaped distal surface 66 of the metaglene component 60. Additionally, or alternatively, the reamed proximal end 92 of the bone graft can define a bore 96 that extends at least partially through the graft along a longitudinal axis A1-A1 to receive the post 64 of the metaglene component 60. A person skilled in the art will recognize other configurations that are possible.

Existing annular cutting tools for resecting bone grafts typically exhibit a lack of durability, inefficient cutting performance, and/or excessive heat generation. For example, conventional tools are typically configured with pyramid-shaped cutting teeth in a hole saw pattern. Pyramid-shaped cutting teeth limit the useful cutting edge of the tool and are prone to premature dulling. Conventional cutting tools also lack features to accumulate morselized bone debris away from the cutting teeth, resulting in bone debris being packed into the tooth geometry and limiting the advance of the saw, i.e., causing it to bind. For example, the operator may be required to make several approaches, such that the tool is withdrawn between approaches to clear the accumulated bone debris before a cut is complete. Some tools generate excessive heat due to frictional contact between the tool and bone that can be detrimental to the viability of the resected bone graft. Still further, existing designs are also prone to overheating, which can limit the length of time for which the tool can be used, among other undesirable results that occur due to a surgical tool overheating. The overheating results from a number of factors, including but not limited to the amount of pressure, contact area, and rotations necessary to achieve a desired resection.

Accordingly, there is a need for improved annular cutting tools having, for example, improved cutting geometry, debris removal features, and a design that limits the amount of heat generated by the tool in use, and related methods of resecting a bone graft using the various embodiments of an annular cutting tool provided for herein, or otherwise derivable from the present disclosures.

SUMMARY

The present disclosure is generally related to annular cutting tools, and represents improvements over existing designs of such tools. Annular cutting tools are used in the medical field to resect a cylindrically-shaped bone graft, e.g., from a humeral head for attachment to a metaglene component in reverse shoulder procedures. However, existing designs for such conventional tools typically exhibit a lack of durability, inefficient cutting performance, and/or excessive heat generation.

As discussed in greater detail below, the provided for embodiments of an annular cutting tool, sometimes referred to as a reamer, can include an annular body having cutting teeth with an improved geometry. The improved geometry exists in various aspects of the tool, including but not limited to the design of the teeth, the design of the cutting body or head on which the teeth are disposed (often cylindrical in design), and the cannulated drill or drill bit disposed within a circumference of the cutting head, or perimeter defined by the shape of the cutting head. For example, with respect to the teeth, in some embodiments, each cutting tooth can include a flared distal tip that is substantially flat to provide a greater cutting surface and greater durability. Alternatively, or additionally, one or more gullets having an extended vertical depth can be disposed between groups of adjacent cutting teeth to facilitate removal of bone debris away from the cutting teeth and thus prevent or reduce binding of the tool during use. Alternatively, or additionally, the cutting body can have a recessed surface portion to reduce the area of direct contact to bone, thus decreasing the amount of frictional heat generated during use. The recessed surface portion can also provide an area in which bone debris can accumulate away from the cutting teeth to prevent, or further reduce, binding of the tool during use. The annular cutting body can also include a centrally-disposed drill bit (e.g., a cannulated drill bit) that can be inserted over a guide pin to align the tool with respect to a target bone in addition to drilling a hole in the bone graft, e.g., to receive a post of the metaglene component.

One exemplary embodiment of an annular cutting tool includes an annular cutting body, a plurality of cutting teeth, a drill bit, and a drive shaft. The annular cutting body has a proximal end, a distal end, and a central portion disposed between the proximal end and the distal end. Further, a central longitudinal axis of the annular cutting body extends from the proximal end to the distal end. The plurality of cutting teeth are disposed at the distal end of the annular cutting body, the teeth extending radially outward beyond the central portion of the annular cutting body with respect to the central longitudinal axis such that the central portion includes a recessed surface area. The drill bit extends distally from the proximal end of the annular cutting body, along the central longitudinal axis. The drive shaft extends proximally from the proximal end of the annular cutting body and is coaxial with the central longitudinal axis of the annular cutting body. In some embodiments, the drill bit can be a cannulated drill bit.

One or more teeth of the plurality of cutting teeth can have a substantially flat distal tip. In some embodiments, the plurality of cutting teeth can extend radially inward from the central portion of the annular cutting body. One or more extended gullets can be located in the central portion of the annular cutting body. Each extended gullet of the one or more extended gullets can be disposed between adjacent teeth of the plurality of cutting teeth, and the one or more extended gullets can have more than one tooth of the plurality of cutting teeth disposed between an adjacent gullet when more than one extended gullet is located in the central portion of the annular cutting body.

The annular cutting body can have one or more cleaning apertures located in the central portion, with such apertures being configured to allow bone debris to pass through the aperture(s). In some such embodiments, at least one cleaning aperture can include a distal terminal end that has an inverted V-shape. An annular protrusion can be disposed at the proximal end of the annular cutting body, which allows the recessed surface area to be bounded by a proximal end of the plurality of cutting teeth and the annular protrusion. One or more blades can be transversely disposed at the proximal end of the annular cutting body.

The drill bit can have a distal cutting tip that includes a plurality of planer cutting surfaces. Some such embodiments can have an interior angle between one or more pairs of the plurality of planer cutting surfaces that is approximately 120 degrees.

The annular cutting body, the drill bit, and the drive shaft can be manufactured as a single unitary body.

Another exemplary embodiment of an annular cutting tool also includes an annular cutting body, a plurality of cutting teeth, a drill bit, and a drive shaft. The annular cutting body has a proximal end and a distal end, with a central longitudinal axis of the annular cutting body extending from the proximal end to the distal end. The plurality of cutting teeth are disposed at the distal end of the annular cutting body. One or more teeth of the plurality of teeth have a flared and substantially flat distal tip. The drill bit extends distally from the proximal end of the annular cutting body, along the central longitudinal axis. The drive shaft extends proximally from the proximal end of the annular cutting body and is coaxial with the central longitudinal axis of the annular cutting body. In some embodiments, the drill bit can be a cannulated drill bit.

In some embodiments, the plurality of cutting teeth can extend radially inward from the annular cutting body. One or more extended gullets can be located in the annular cutting body. Each extended gullet of the one or more extended gullets can be disposed between adjacent teeth of the plurality of cutting teeth, and the one or more extended gullets can have more than one tooth of the plurality of cutting teeth disposed between an adjacent gullet when more than one extended gullet is located in the annular cutting body.

The annular cutting body can have one or more cleaning apertures located in the annular cutting body, with such apertures being configured to allow bone debris to pass through the aperture(s). In some such embodiments, at least one cleaning aperture can include a distal terminal end that has an inverted V-shape. An annular protrusion can be disposed at the proximal end of the annular cutting body such that a recessed surface area of the annular cutting body is bounded by a proximal end of the plurality of cutting teeth and the annular protrusion. One or more blades can be transversely disposed at the proximal end of the annular cutting body.

The drill bit can have a distal cutting tip that includes a plurality of planer cutting surfaces. Some such embodiments can have an interior angle between one or more pairs of the plurality of planer cutting surfaces that is approximately 120 degrees.

The annular cutting body, the drill bit, and the drive shaft can be manufactured as a single unitary body.

One exemplary method of resecting a bone graft includes positioning an annular cutting tool with respect to a bone. The annular cutting tool has a drill bit and an annular cutting body that is disposed circumferentially around at least a portion of the drill bit. Further, the annular cutting body has a plurality of cutting teeth disposed at a distal end of the body. The method further includes applying a torque to the annular cutting tool to cause the plurality of cutting teeth to rotate about a longitudinal axis of the cutting tool. The method further includes distally advancing the annular cutting tool into the bone while the torque is being applied to cause the plurality of cutting teeth to contact and cut the bone, thereby defining a bone graft. During distal advancement, a portion of the annular cutting body directly proximal to the plurality of cutting teeth does not contact the bone from which the bone graft is being removed. Further, distally advancing the annular cutting tool into the bone while the torque is being applied causes the drill bit to ream a hole in the defined bone graft.

The annular cutting tool can be configured in a manner similar to described above with respect to various exemplary embodiments, or as otherwise provided for throughout the present disclosure. For example, the drill bit can be cannulated. In such embodiments, positioning the annular cutting body can include distally inserting the cannulate drill bit over a guide pin that extends from the bone. By way of further non-limiting example, the plurality of cutting teeth can extend radially outward beyond a central portion of the annular cutting body with respect to the central longitudinal axis of the cutting tool, thereby defining a recessed surface area on the central portion, proximal to the plurality of cutting teeth. In some such embodiments, one or more teeth of the plurality of cutting teeth can have a substantially flat distal tip.

Portions of the bone that are cut can pass through one or more cleaning apertures located on the annular cutting body. In some embodiments, distally advancing the annular cutting tool into bone while the toque is being applied can further cause one or more blades of the annular cutting tool disposed proximal of the plurality of cutting teeth to shape a proximal surface of the bone graft. The methods provided for herein can also include additional steps that are included as part of a resection procedure, such as using resection guides and oscillating saws to form and remove the graft, as provided for in greater detail below. Distally advancing the annular cutting tool can result in formation of the bone graft in a single distal advancement of the annular cutting tool, without having to pull back the annular cutting tool.

BRIEF DESCRIPTION OF THE DRAWINGS

The accompanying drawings, which are incorporated herein and constitute part of this specification, illustrate exemplary embodiments, and together with the general description given above and the detailed description given below, serve to explain the features of the various embodiments.

DETAILED DESCRIPTION

Figure 1A:
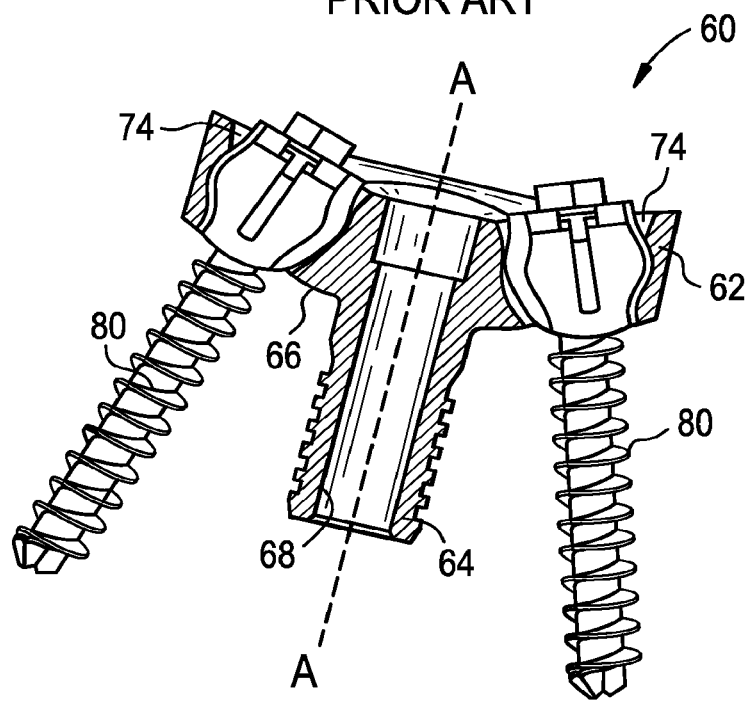
FIG. 1A is a side, partial cross-sectional view of one example of a shoulder joint implant of the prior art.
Figure 1B:
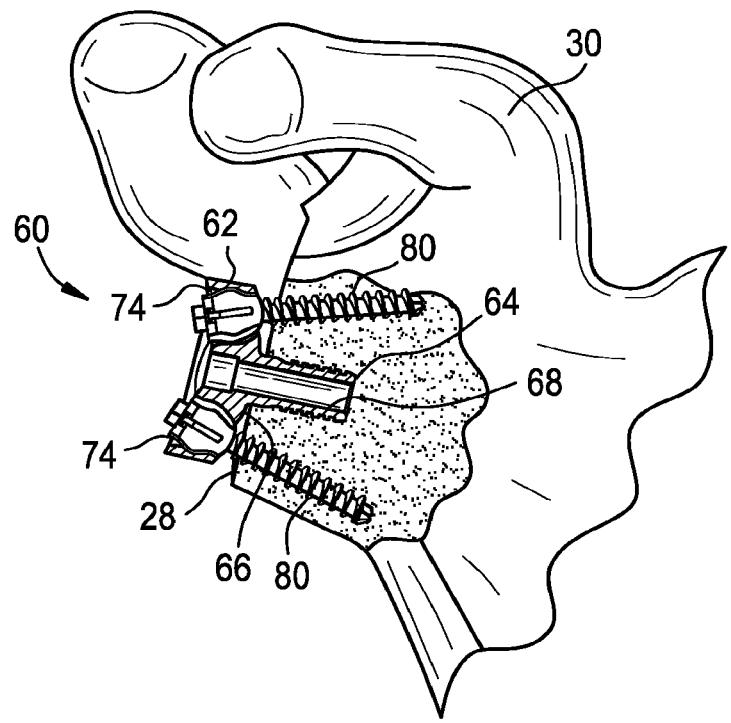
FIG. 1B is a schematic side view of the shoulder joint implant of FIG. 1A coupled to a scapula.

Certain exemplary embodiments will now be described to provide an overall understanding of the principles of the structure, function, manufacture, and use of the annular cutting tools and methods disclosed herein. One or more examples of these embodiments are illustrated in the accompanying drawings. Those skilled in the art will understand that the annular cutting tools and methods specifically described herein and illustrated in the accompanying drawings are non-limiting exemplary embodiments and that the scope of the present disclosure is defined solely by the claims. The features illustrated or described in connection with one exemplary embodiment may be combined with the features of other embodiments. Such modifications and variations are intended to be included within the scope of the present disclosure. Sizes and shapes of the annular cutting tools, and the components thereof, can depend on a variety of factors, including but not limited to an anatomy of the subject (i.e., patient) on which the annular cutting tool will be used, the size and configuration of auxiliary components with which the annular cutting tool will be used (e.g., a power drill), the methods and procedures in which the annular cutting tool will be used, and the preferences of the surgeon operating the annular cutting tool and/or otherwise performing the related procedure(s).

A number of terms may be used throughout the disclosure interchangeably but will be understood by a person skilled in the art. Additionally, to the extent that linear or circular dimensions are used in the description of the disclosed devices and methods, such dimensions are not intended to limit the types of shapes or sizes of such tools. A person skilled in the art will recognize that an equivalent to such linear and circular dimensions can be easily determined for any geometric shape (e.g., references to widths and diameters being easily adaptable for circular and linear dimensions, respectively, by a person skilled in the art). Additionally, to the extent that terms are used in the disclosure to describe a direction, orientation, and/or relative position of the disclosed tools and components thereof and/or for performing a disclosed method of resecting a bone graft using the embodiment annular cutting tools, such terms are not intended to be limiting. For example, a person skilled in the art will recognize that terms of direction, orientation, and/or relative position (e.g., proximal, distal, medial, lateral, etc.) can be used interchangeably depending, at least in part, on the perspective view of the surgeon or other operator.

The present disclosure is generally related to annular cutting tools, and represents improvements over existing designs of such tools. Various embodiments of an annular cutting tool provided for herein can exhibit improved durability, cutting performance, and/or reduced heat generation during use.

The provided for embodiments of an annular cutting tool can include an annular cutting body having cutting teeth with an improved geometry. The improved geometry exists in various aspects of the tool, including but not limited to the design of the teeth, the design of the cutting body or head on which the teeth are disposed (often cylindrical in design), and the cannulated drill or drill bit disposed within a circumference of the cutting head, or perimeter defined by the shape of the cutting head. For example, with respect to the teeth, in some embodiments, one or more of the cutting teeth can include a flared distal tip that is substantially flat to provide a greater cutting surface and greater durability. Alternatively, or additionally, one or more gullets having an extended vertical depth can be disposed between groups of adjacent cutting teeth to facilitate removal of bone debris away from the cutting teeth and thus prevent or reduce binding of the tool during use. Alternatively, or additionally, the annular cutting body can have a recessed surface portion to reduce the area of direct contact to bone and thus decrease the amount of heat generated during use. The recessed surface portion can also provide an area in which bone debris can accumulate away from the cutting teeth to prevent or reduce binding of the tool during use. The annular cutting body can also include a cannulated drill bit configured for insertion over a guide pin to align the tool with respect to target bone and for drilling a hole in a resected bone graft, e.g., to receive a post of a metaglene component.

Although the disclosures provided for herein are generally directed to use of an annular cutting tool or reamer for resecting a bone graft from a humeral head for attachment to a metaglene component in reverse shoulder procedures, one skilled in the art will recognize that the annular cutting tools provided for herein, or otherwise derivable from the present disclosure, can be used to resect bone grafts from other parts of a patient's body or allograft for use in other surgical procedures. A person skilled in the art will also understand how the disclosures provided for herein can be adapted for use in cutting out cylindrically-shaped or annularly-shaped objects from other materials or substrates (e.g., wood, plastic, etc.). Accordingly, the present disclosures extend to uses beyond the medical field, including but not limited to manufacturing, construction, building, and other fields that involve cutting with an annular cutting tool or other cutting instrument.

Figure 3A:
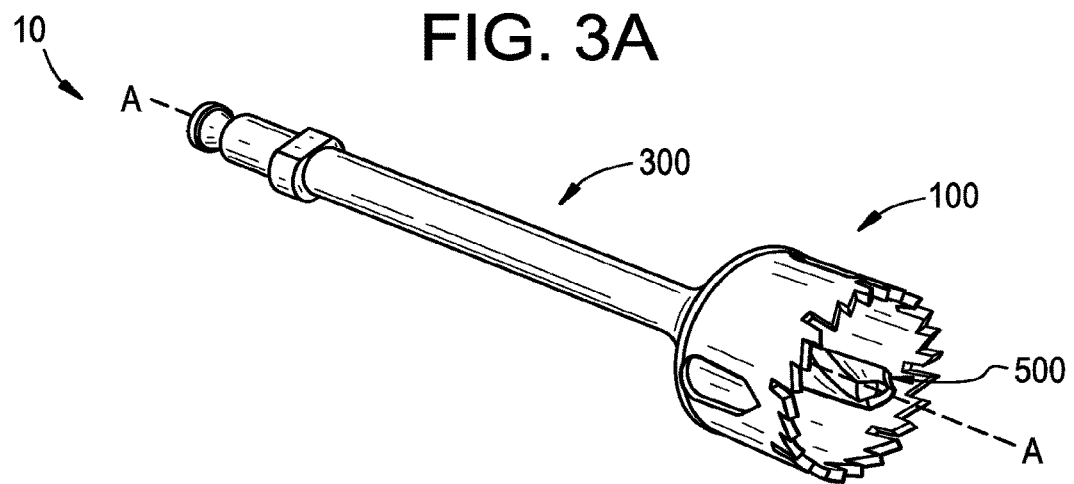
FIG. 3A is a perspective view of one exemplary embodiment of an annular cutting tool, the tool including an annular cutting body, a drive shaft, and a drill bit.
Figure 3B:
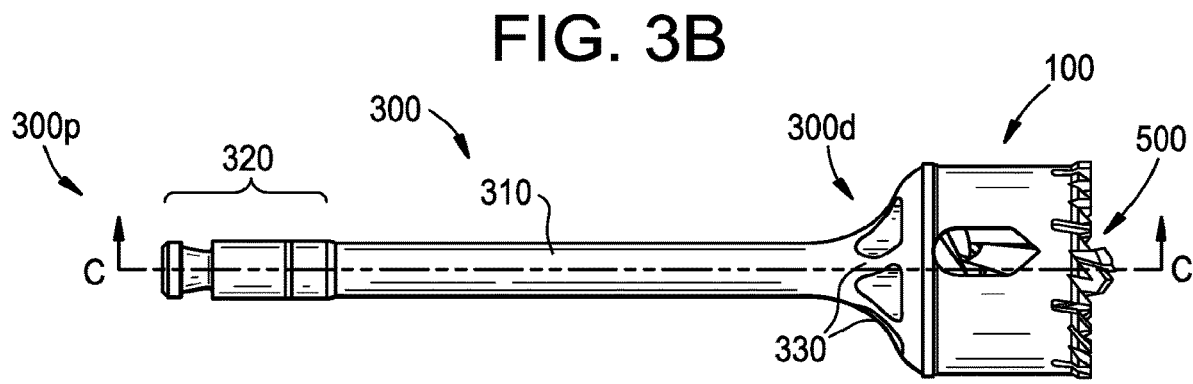
FIG. 3B is a side view of the annular cutting tool of FIG. 3A.
Figure 3C:
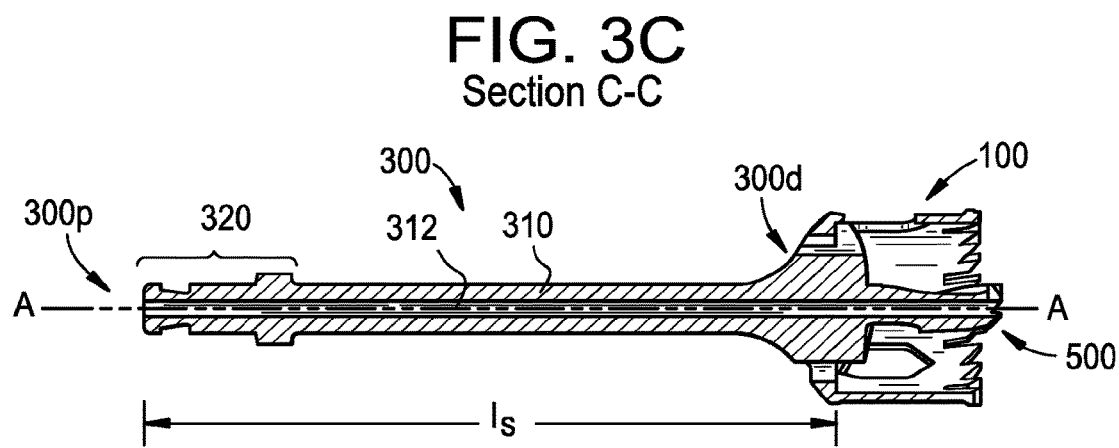
FIG. 3C is a side, cross-sectional view of the annular cutting tool of FIG. 3B taken along line C-C.

FIGS. 3A, 3B, and 3C are schematic illustrations of one exemplary embodiment of an annular cutting tool 10, sometimes referred to herein as a reamer or instrument. The reamer 10 includes an annular cutting body 100, a drive shaft 300, and a cannulated drill bit 500. As shown, the annular cutting body 100, the drive shaft 300, and the cannulated drill bit 500 can be coaxially aligned along a central longitudinal axis A-A of the reamer 10. In some embodiments, the annular cutting body 100, the drive shaft 300, and the cannulated drill bit 500 can be manufactured as a single unitary body. Techniques for such manufacturing can include any known technique for manufacturing a surgical instrument, although the present disclosure provides some features that are particularly well-adapted for use using three-dimensional (3-D) printing techniques (e.g., the design of cleaning apertures 104, and more particularly the triangular shape proximate to teeth 110). Alternatively, in some embodiments, the annular cutting body 100, the drive shaft 300, the cannulated drill bit 500, or any combination thereof can be manufactured separately and then welded or otherwise assembled together to form the reamer 10. Such techniques for manufacturing are likewise known to those skilled in the art and/or can be adapted for use in view of the present disclosures. A benefit to the single unitary body construction is that it can eliminate a need for welds or additional components to hold pieces together, thereby decreasing potential failure points in the design.

A power drill or other rotary power tool (not shown) can be attached to the drive shaft 300. The drive shaft 300 transfers distal pressure and torque applied by the power drill to the annular cutting body 100 and the cannulated drill bit 500. As the spinning reamer 10 is distally advanced into bone, the annular cutting body 100 cuts a cylindrically-shaped bone graft into the bone and the drill bit 500 drills a hole into the bone graft. The annular cutting body 100 can also be configured to ream the proximal surface of the bone graft to have a concave, convex, or other desired shape. After removing the reamer 10 from the bone, an oscillating saw or other linear cutting tool (not shown) can be used to make a lateral cut across the distal end of the bone graft so that the graft can be resected from the bone.

As shown in FIGS. 3B and 3C, the drive shaft 300 has a substantially linear body 310 that extends coaxially along the central longitudinal axis A-A of the reamer 10. In the illustrated embodiment, the drive shaft 300 has a substantially cylindrical or rod-shaped body 310. In some embodiments, the drive shaft 300 can have an elongated body with a rectangular or other geometric cross-sectional profile. The cross-sectional dimensions of the drive shaft 300 (e.g., diameter, width, height, etc.) and/or its cross-sectional profile can remain constant or change along the length of the shaft. As shown in FIG. 3C, the drive shaft 300 can be a cannulated drive shaft having an open-ended channel or throughbore 312 that extends along the longitudinal axis A-A of the reamer 10. The channel 312 of the drive shaft 300 can be used for a variety of purposes. For example, as described in greater detail below, the channel 312 of the drive shaft 300 can be used to receive a guide pin for aligning the reamer 10 with respect to a bone from which to resect the bone graft.

The drive shaft 300 can have any desired length. For example, in some embodiments, the drive shaft 300 can have a length $l_s$ that allows the annular cutting body 100 to access a target bone percutaneously while the power drill remains outside the patient's body. Alternatively, or additionally, the drive shaft 300 can have a length $l_s$ that provides the operator with sufficient leverage or torque to cut into the bone. In some embodiments, the drive shaft 300 can have a length $l_s$ approximately in a range between about 25 mm to about 200 mm. For example, the length $l_s$ of the drive shaft 300 can be about 60 mm.

The proximal end 300p of the drive shaft 300 can include a shank 320 configured to attach the reamer 10 to a chuck of a power drill (or other coupling mechanism of a rotary power tool). One skilled in the art will recognize that various types of shanks can be used to attach the reamer 10 to a power drill, such as a 3-flat shank, a reduced shank, or a tang shank. The distal end 300d of the drive shaft 300 can be coupled to the proximal end 100p of the annular cutting body 100. For example, as shown in the illustrated embodiment of FIG. 3B, the drive shaft 300 can include radial support arms 330 that extend outward from the distal end 300d of the shaft to an outer perimeter of the annular cutting body 100. The illustrated shape of the arms 330, which is angled with respect to the central longitudinal axis A-A, can reduce, or even eliminate, the need for additional supports for the cutting portions of the tool.

As shown in FIGS. 4A-4E, the annular cutting body 100 can include a number of features for improving durability, cutting performance, and/or reducing heat during use of the reamer 10. The annular cutting body 100 is generally ring shaped having a proximal end 100p and a distal end 100d. The central longitudinal axis of the annular cutting body 100 between the proximal and distal ends is substantially coaxial with the axis A-A of the reamer 10. The interior of the annular cutting body 100d can have any suitable dimensions depending, at least in part, on the desired size of the resected bone graft. For example, to resect a cylindrically-shaped bone graft suitable for attachment to a metaglene component (e.g., 60) to fill in an eroded space in the glenoid, the interior of the annular cutting body 100 can have a diameter $d_c$ approximately in a range between about 20 mm to about 40 mm and a length $l_c$ approximately in a range between about 15 mm to about 30 mm. For example, the interior of the annular cutting body 100 can have a diameter $d_c$ that is about 27 mm and a length $l_c$ that is about 23 mm.

Cutting teeth 110 are disposed along the distal end 100d of the annular cutting body 100 in a ring-shaped pattern for cutting a cylindrically-shaped bone graft. The distal tips 112 of the cutting teeth 110 can be substantially flat to reduce the risk of premature dulling of the teeth, thus increasing their durability. The tips 112 are substantially flat because they do not terminate into a point. For example, in the illustrated embodiment of FIGS. 4C and 4D, an individual cutting tooth 110a is configured in the shape of a saw tooth having a substantially flat distal cutting tip 112a. As shown, the cutting tooth 110a has a substantially planar rake face 116a and a substantially planar back 118a (i.e., the hypotenuse of the tooth). The rake face 116a can ramp upward or extend substantially vertical from the proximal root 114a of the tooth and intersect with the back 118a of the tooth 110a to form a substantially flat cutting tip 112a. The substantially flat-tipped cutting teeth can exhibit less premature dulling of the teeth as compared to cutting teeth having pointed or pyramidal tips. Although the illustrated cutting teeth 110 is shown in the shape of a saw tooth, a person skilled in the art will recognize that the cutting teeth 110 can be adapted to have different shapes, and at least some such shapes can also include a substantially flat distal tip as provided for herein.

Figure 4A:
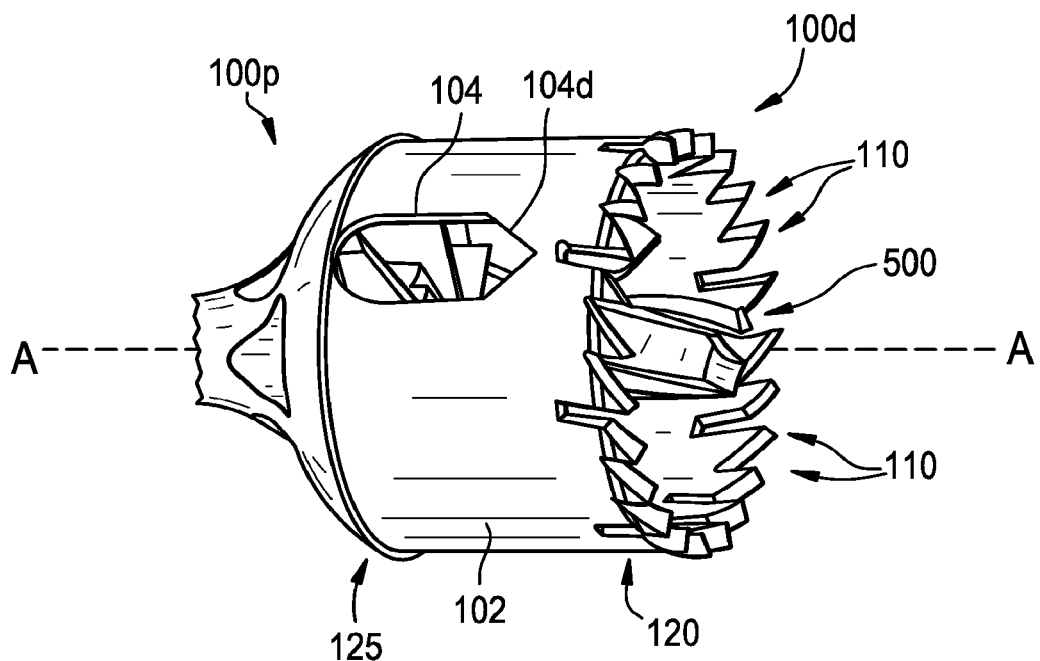
FIG. 4A is a side perspective view of the annular cutting body of FIG. 3A.

In some embodiments, the distal tips 112 of the cutting teeth 110 can be configured to flare out radially with respect to the annular cutting body 100. For example, as shown in FIG. 4D, the flared distal tip 112a of the cutting tooth 110a has a width $w_1$ that is greater than a width $w_2$ at a proximal root 114a of the tooth. In some embodiments, the flared distal tip 112a can have a width $w_1$ approximately in a range between about 1 mm to about 3 mm and the proximal root 114a can have a width $w_2$ approximately in a range between about 0.5 mm to about 2 mm. For example, the flared distal tip 112a of the cutting tooth 100a can have a width $w_1$ equal to approximately 1.8 mm and the proximal root 114a of the tooth can have a width $w_2$ equal to approximately 1.3 mm.

Collectively, the flared distal tips 112 of the cutting teeth 110 can form a lateral-facing lip, also referred to as a radial lip, 120 about the distal end 100d of the annular cutting body 100. The lateral-facing lip 120 effectively defines a recessed or stepped-down surface area, also referred to as a central portion of the annular cutting body, 102 proximal to the cutting teeth 110. For example, as shown in the FIGS. 4A and 4B, the flared distal tips 112 of the cutting teeth 110 can protrude laterally or radially outward from the distal end 100d of the annular body 100 to form a recessed surface area 102 in the exterior of the annular body. In some embodiments, an annular protrusion 125 can be defined at the proximal end 100p of the annular body 100 such that the recessed surface area 102 is bounded between the lateral-facing lip 120 and the annular protrusion 125. Like the lateral-facing lip 120, the annular protrusion 125 protrudes laterally or radially outward from the proximal end 100p of the annular body 100 to form, or otherwise define, the recessed surface area 102 in the exterior of the annular body.

During use, direct contact between the lateral-facing exterior of the annular cutting body 100 and a bone under resection can be generally limited to the surface area of the lateral-facing lip 120, and optionally the annular protrusion 125. The design of the present tool 10 is such that direct contact with bone by the recessed surface area 102 during use is limited or altogether eliminated. By reducing lateral surface contact of the annular cutting body 100 with a bone under resection, the heat generated due to friction during use of the reamer 10 can be reduced. Reduced heat generation can, among other benefits, improve the viability of the resected bone graft. Alternatively, or additionally, the recessed surface area 102 can also provide a space in which bone debris can accumulate away from the cutting teeth to prevent or reduce binding of the tool during use and thereby improving cutting performance.

Although the illustrated embodiment shows the flared distal tips 112 of the cutting teeth 110 protruding radially outward to form a recessed surface area 102 in the exterior of the annular body, a person skilled in the art will recognize the flared distal tips 112 can be configured to protrude radially inward such that a recessed surface area can be formed in an interior of the annular cutting body 100. Alternatively, or additionally, the flared distal tips 112 of the cutting teeth 110 can be configured to protrude radially outward and inward to form recessed surface areas in the exterior and interior of the annular cutting body 112.

Figure 4B:
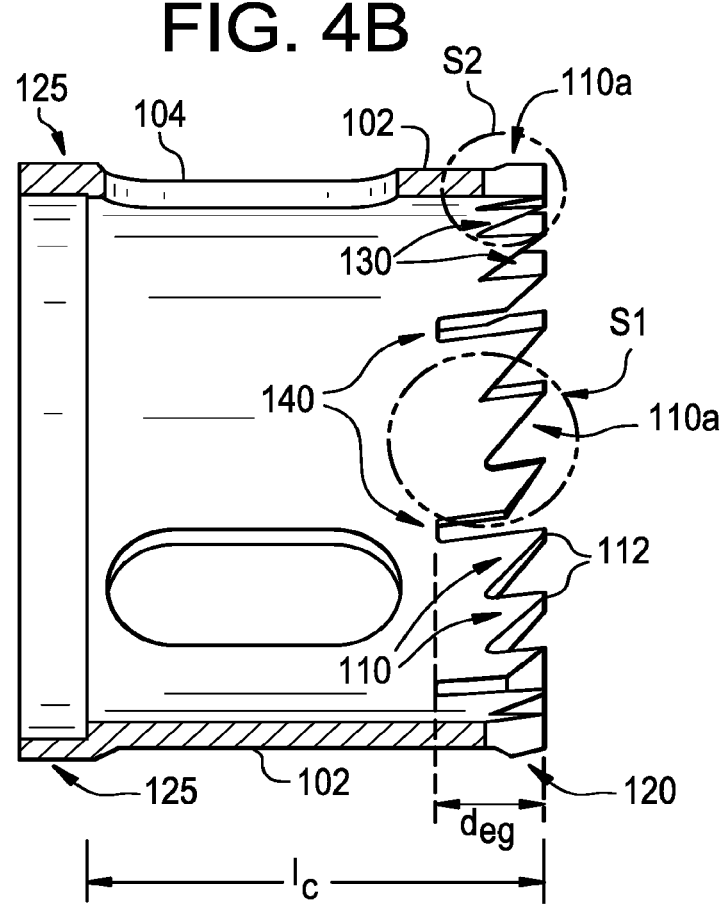
FIG. 4B is a side, partial cross-sectional view of the annular cutting body of FIG. 4A, although a cleaning aperture shown in FIG. 4B has a different shape than a cleaning aperture shown in FIG. 4A.
Figure 4C:
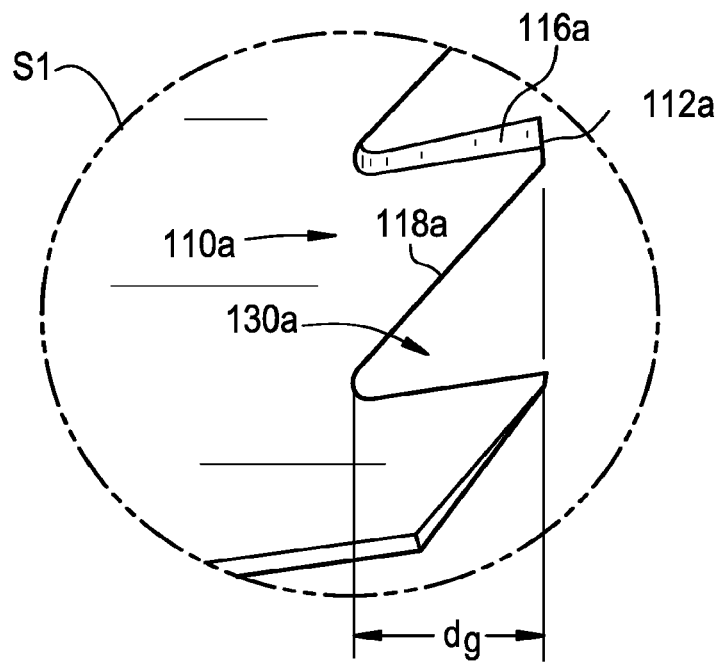
FIG. 4C is a detailed view of a portion of the annular cutting body of FIG. 4B identified as "S1," the portion illustrating a cutting tooth having a saw tooth shape.
Figure 4D:
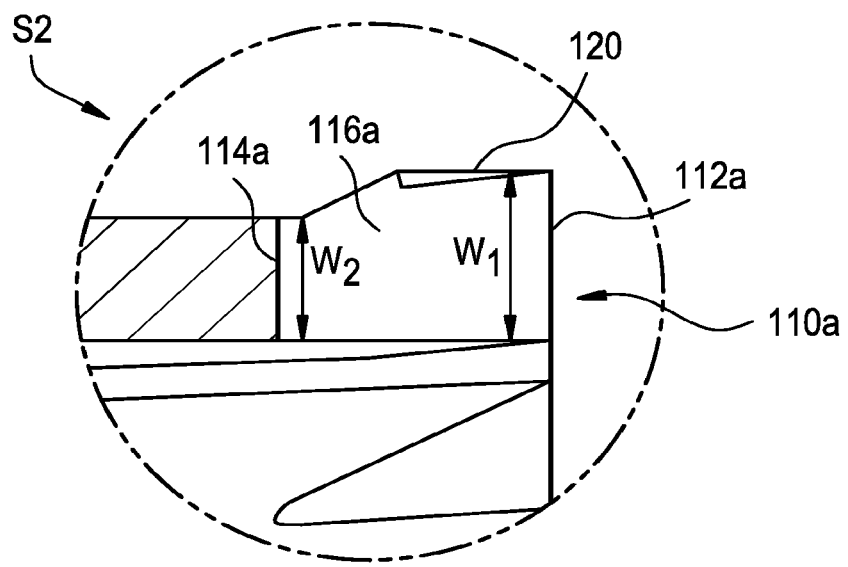
FIG. 4D is a detailed view of a portion of the annular cutting body of FIG. 4B identified as "S2," the portion illustrating a cutting tooth having a flared distal tip.
Figure 4E:
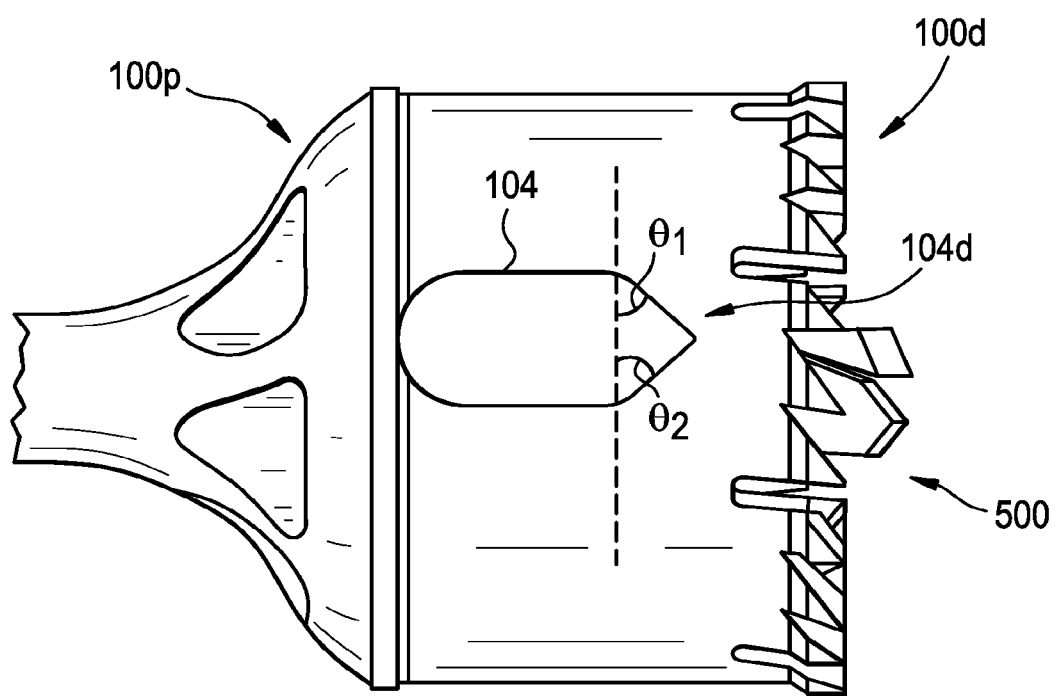
FIG. 4E is a side view of the annular cutting body of FIG. 4A.

As shown in FIGS. 4B and 4C, gullets 130 are defined between adjacent cutting teeth 110. In conjunction with the present disclosure, a gullet is a rounded region located at the base of a cutting tooth that provides a passageway to divert bone debris away from the teeth 110 and/or the drill bit 500, and thus prevent clogging. The depth of a gullet typically extends from a base of the gullet to the tip of an adjacent tooth. In some embodiments, the gullets 130 can be configured to have a vertical depth that is deeper than gullets defined in conventional annular reamers. For example, as shown in FIG. 4C, an individual gullet 130a can have a depth $d_g$ approximately in a range between about 1 mm to about 4 mm. For example, the gullet 130a can have a depth $d_g$ that is about 2.7 mm. Deeper gullet depths can improve the ability of the reamer 10 to more effectively divert bone debris away from cutting teeth 110 and prevent clogging, although the size of the gullet is balanced against providing enough strength for the tool 10 to operate. The present disclosure allows for gullet sizes that both improve the ability to remove debris away from cutting aspects of the tool 10 while maintaining an integrity of the tool. In some embodiments, the deeper gullet depths can be useful to reduce the number of approaches that an operator makes before a cut is complete and to withdraw the reamer between approaches to clear the accumulated bone debris. In some embodiments, the gullets 130 can divert bone debris from the cutting teeth 110 into the recessed or stepped down surface area 102 proximal to the cutting teeth. Debris can also pass through openings 230 disposed between blades 200, as described in greater detail with respect to FIGS. 5A and 5B.

Alternatively, or additionally, as shown in FIGS. 4A and 4B, one or more extended gullets 140 can be defined between groups of adjacent cutting teeth 100 to have a vertical depth $d_{eg}$ that is greater than the depth $d_g$ of the gullets 130. In some embodiments, each of the extended gullets 140 can have a vertical depth $d_{eg}$ that is greater than the depth $d_g$ of the gullets 130 by a factor approximately in the range between about 1.5 and about 6. For example, the extended gullets 140 can have a vertical depth $d_{eg}$ that is greater than the depth $d_g$ of the gullets 130 by a factor of approximately 2. The one or more extended gullets 140, in lieu of or in conjunction with the gullets 130, can prevent, or at least reduce, the accumulation of bone debris on the cutting teeth 110. In some embodiments, the extended gullets 140 can divert bone debris from the cutting teeth 110 into the recessed or stepped down surface area 102 proximal to the cutting teeth. In the illustrated embodiment, an extended gullet 140 is disposed between groups of three cutting teeth 110. In some embodiments, an extended gullet 140 can be disposed between groups having more or less than three adjacent cutting teeth (e.g., 2, 4, 5, etc.). In some embodiments, a total of eight (8) extended gullets 140 can be defined between groups of adjacent cutting teeth 110. In some embodiments, more or less than a total of eight (8) extended gullets 140 can be disposed between groups of adjacent cutting teeth 110.

In some embodiments, the annular cutting body 100 can define one or more cleaning apertures or holes 104, sometimes referred to herein as flushing apertures or holes. For example, as shown in FIGS. 4A and 4B, the cleaning apertures 104 can be defined between the proximal and distal ends 100p, 100d of the annular cutting body 100. The cleaning apertures 104 can be configured to allow bone debris to exit from an interior to an exterior of the annular cutting body 100, or vice versa, from an exterior to an interior of the annular cutting body. In some embodiments, the cleaning apertures 104 can be defined to extend through a recessed (or stepped down) surface area 102 of the annular body. Thus, bone debris that accumulates on a side that opposes the recessed surface area 102 can exit through the cleaning apertures 104 and accumulate within the recessed surface area 102. As discussed above, allowing bone debris to accumulate within a recessed surface area 102 can reduce friction and thus heat generated by the reamer 10. The clean apertures 104 can also be useful to prevent or reduce binding of the tool during use and thereby increase cutting performance.

The cleaning apertures 104 can have any desired shape. For example, as shown in FIGS. 4A and 4B, cleaning apertures 104' can be an elliptical or pill-shaped aperture. In the illustrated embodiment of FIGS. 4A and 4E, the cleaning apertures 104 can be further defined to have an inverted V-shaped end 104d. Such a design can be particularly helpful when manufacturing the reamer 10 using a fabrication technique such as additive manufacturing, or other three-dimensional (3D) printing techniques. The inverted V-shaped end 104d helps reduce, or altogether eliminate, the need for additional support structures that are sometimes required inside of apertures or holes defined in 3D-printed objects. Such additional support structures are usually removed from the apertures in a post processing step, thereby increasing the cost of manufacture.

In the illustrated embodiment, the V-shaped end 104d can be defined opposite a pair of distal-facing angles $\theta_1$ and $\theta_2$ that are approximately equal to about 45 degrees each. In some embodiments, the V-shaped end 104d can be characterized by one or more distal-facing angles $\theta_1$ and/or $\theta_2$ that are respectively equal to an oblique angle approximately in a range of about 35 degrees to about 65 degrees, thereby avoiding the need of support structures. In some embodiments, three cleaning holes 104 can be defined to be approximately evenly spaced apart around a circumference of the annular body 100. In some embodiments, there can be more or less than three cleaning holes 104 (e.g., 1, 2, 4, etc.).

Figure 5A:
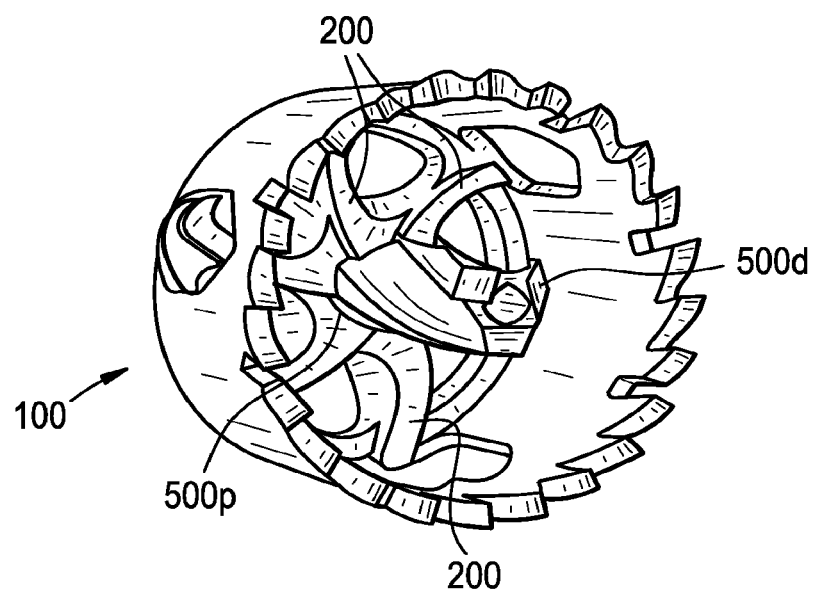
FIG. 5A is a front perspective view of the annular cutting body of FIG. 4A.
Figure 5B:
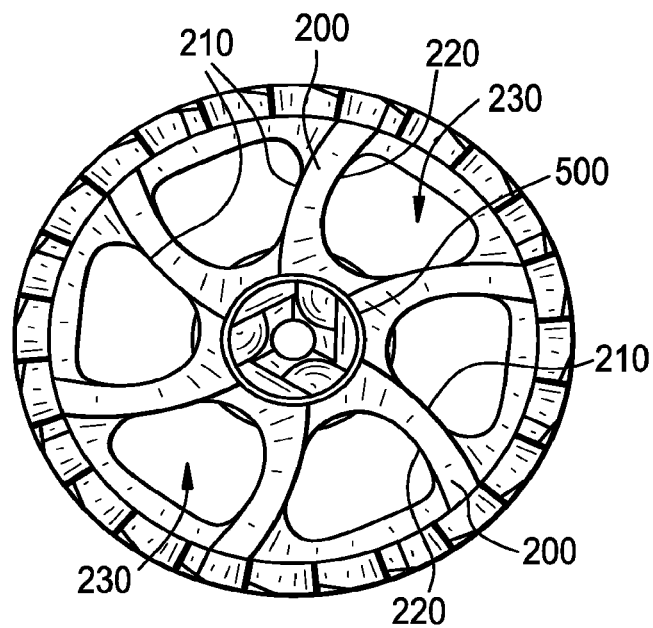
FIG. 5B is a front view of the annular cutting body of FIG. 5A that illustrates multiple surface reaming blades.

As shown in FIGS. 5A and 5B, one or more surface reaming blades 200 can be approximately transversely disposed at the proximal end 100p of the annular cutting body 100. The blades 200 can be configured to ream a proximal surface of a cylindrically-shaped bone graft cut by the teeth 110 of the annular cutting body 100 into any desired geometrical shape. For example, in some embodiments, when the annular cutting body 100 is spinning, the blades 200 can ream the proximal surface of a bone graft to have a concave, convex, or flat surface. In the illustrated embodiment, six (6) surface reaming blades 200 are approximately evenly disposed around the drill bit 500 (i.e., each is about 60 degrees apart from adjacent blades 200) and are configured to ream a concave shape into the proximal surface of a bone graft (e.g., for mating with the generally convex-shaped distal surface 66 of the metaglene component 60 of FIG. 1A). In some embodiments, more or less than six surface reaming blades 200 can be configured at the proximal end of the annular cutting body (e.g., 1, 2, . . . , 5, 7, etc.). In some instances, the blades 200 may not be approximately evenly disposed around the drill bit 500, thus allowing for even more variations in the types of surfaces that can be formed by the blades 200.

As shown in the illustrated embodiment, the surface reaming blades 200 can extend radially outward from the central longitudinal axis A-A to an inner wall 106 of the annular cutting body 100 in a spiral pattern. Each blade can have an arcuate-shaped leading reaming edge 210, and an arcuate-shaped trailing edge 220. The leading reaming edge 210 of the blade 210 can be more distal than the trailing edge 220 of the blade 210. Bone debris caused by the blades 200 reaming the proximal surface of a bone graft can be diverted from the interior of the annular cutting body through the openings 230 defined between the blades 200. The shape of the openings 230 can be defined by the shape of the blades 210, although in some embodiments the shape of the openings 230 can be independent of the shape of the blades. A person skilled in the art will recognize that the number, topology, and/or pattern of the blades 200 can be configured in different ways to ream a concave or other desired geometrical shape into the proximal surface of a bone graft. In some embodiments, the surface reaming blades 200 can be defined on a distal-facing surface of one or more of the radial support arms 330 of the drive shaft 300 that extend into the interior of the annular cutting body 100.

Alternatively, or additionally, a cannulated drill bit 500 can be approximately centrally disposed within the annular cutting body 100, i.e., within a circumference of the cutting head, or perimeter defined by the shape of the cutting head. For example, as shown in FIGS. 5A and 5B, a cannulated drill bit 500 can have a proximal end 500p and a distal end 500d and extend distally from the proximal end 100p of the annular cutting body 100 along the central longitudinal axis A-A. A hollow opening that forms the cannulated portion of the drill bit 500 can be formed along the central longitudinal axis A-A. Alternatively, the drill bit 500 can be solid, and thus no cannulation exists. In some embodiments, the distal end 500d of the cannulated drill bit 500 can extend distally up to or past the distal end 100d of the annular cutting body 100 such that the drill bit can cut a central hole that extends through the cylindrically-shaped bone graft, thus forming an annular shaped bone graft. In some embodiments, the distal end 500d of the cannulated drill bit 500 can terminate proximal to the distal end 100d of the annular cutting body 100 such that the drill bit can cut a central hole that extends partially through the cylindrically-shaped bone graft.

Figure 6A:
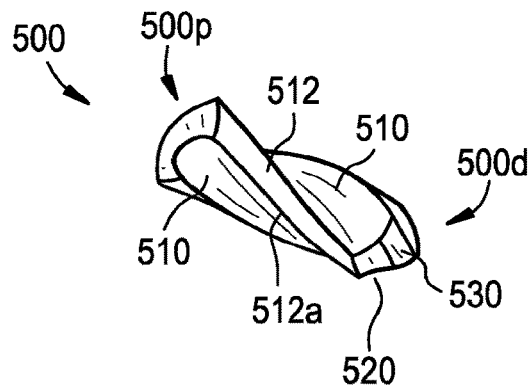
FIG. 6A is a side perspective view of the drill bit of FIG. 3A.
Figure 6B:
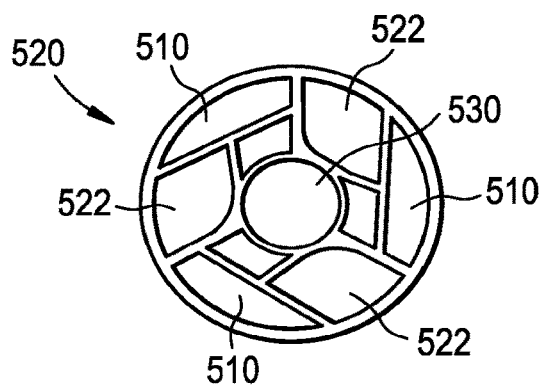
FIG. 6B is a front view of the drill bit of FIG. 6A.
Figure 6C:
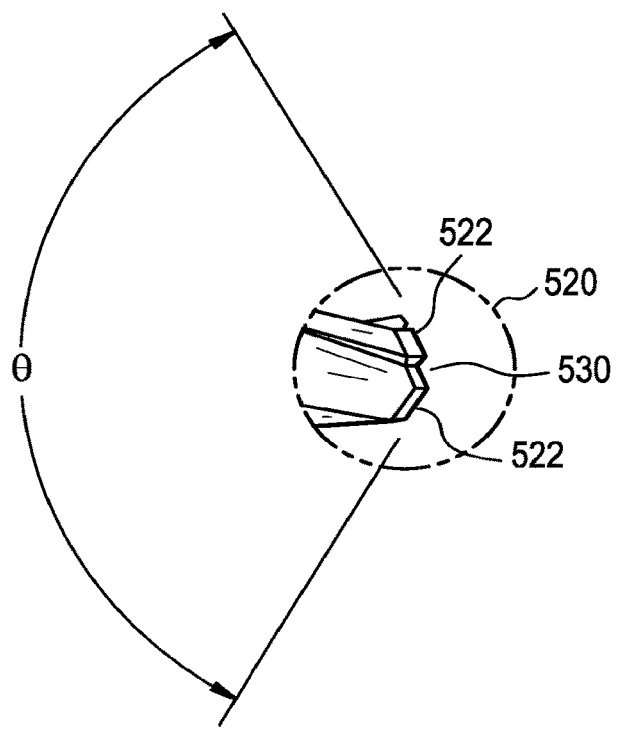
FIG. 6C is a detailed side view of the drill bit of FIG. 6A.

As shown in FIGS. 6A, 6B, and 6C, the drill bit 500 has an elongated body that extends coaxially along the central longitudinal axis A-A of the reamer 10. The drill bit 500 can have two or more flutes 510, or twisted grooves, separated by two or more twisted lands 512 having a leading cutting edge 512a. The lands 512 and flutes 510 extend longitudinally between a proximal end 500p and a distal end 500d of the drill bit to respectively cut and divert bone debris from a drilled hole away from the distal cutting tip 520 of the drill bit 500. In the illustrated embodiment, the drill bit 500 includes three twisted flutes 510 separated by three twisted lands 512, with the flutes 510 having a concave configuration. In the illustrated embodiment, a longitudinal surface of each twisted land 512 extends across approximately 90 degrees of a circumference of the drill bit 500 from the proximal end 500p to the distal end 500d. A person skilled in the art, in view of the present disclosures, will appreciate that the spiraling shape of the teeth can extend across more or less of a circumference of the drill bit 500, such as approximately in the range of between about 10 degrees of a circumference of the drill bit 500 and about 180 degrees of a circumference of the drill bit 500.

In the illustrated embodiment, the lands 512 terminated at the distal end 500d to in a flared manner to form the distal cutting tips 520. The distal cutting tip 520 of the drill bit 500 can include one or more planar cutting surfaces 522, which as shown can have a substantially diamond-shaped cross section. In the illustrated embodiment, the distal cutting tip 520 includes three planar cutting surfaces 522 that are approximately evenly spaced apart from each other. As shown in FIG. 6C, the planar cutting surfaces 522 can be configured to define an interior angle θ with respect to one another. In some embodiments, the planar cutting surfaces 522 can be configured to form an interior angle θ approximately in the range between about 10 degrees and about 150 degrees. For example, the interior angle θ can be equal to approximately 120 degrees. While in the illustrated embodiment there are three flutes 510, three lands 512, and three distal cutting tips 520 having a substantially diamond-shaped cross section, other shapes of the cutting tip and/or any other number of flutes, lands, and tips (e.g., 1, 2, 4, 5, 6, etc.) can also be used.

The design of the flutes 510, lands 512, and cutting tips 520 of the drill bit 500 allows for improved reaming action, by decreasing heat generation and reducing possible binding, similar to enhancements provided in conjunction with the teeth 110. Additionally, a depth achieved by the design of the drill bit 500 allows for a depth that is approximately three times deeper than traditional designs.

In some embodiments, the drill bit 500 can be a cannulated drill bit having an open-ended channel or throughbore 530 that extends along the central longitudinal axis A-A of the reamer 10. The cannulated drill bit 500 can be used for a variety of purposes. For example, as described in greater detail below, the longitudinal channel 530 of the cannulated drill bit 500 can be inserted over a guide pin to align the tool with respect to a target bone in addition to drilling a hole in the bone graft, e.g., to receive a post of the metaglene component.

Figure 2A:
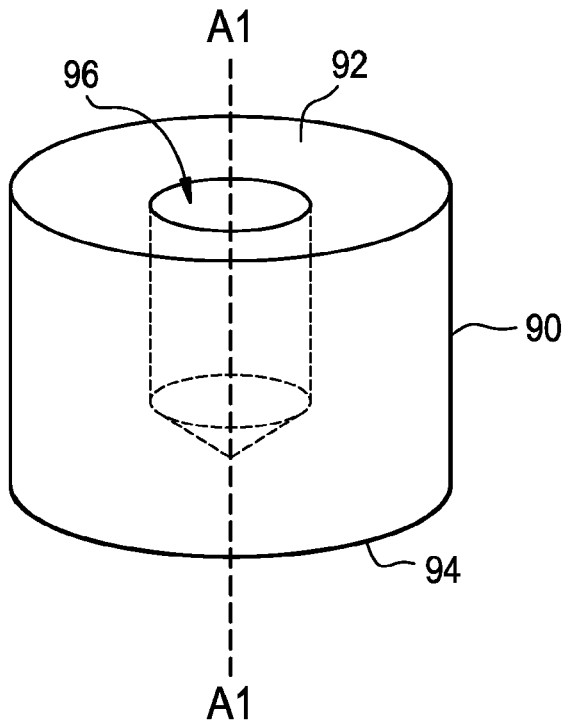
FIG. 2A is a perspective view of one example of a cylindrically-shaped bone graft.
Figure 2B:
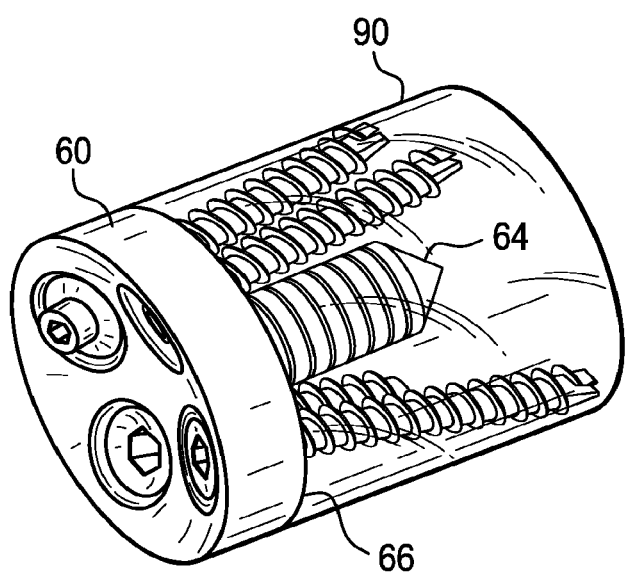
FIG. 2B is a perspective view of the bone graft of FIG. 2A attached to the exemplary shoulder joint implant of FIG. 1A.

As discussed above with respect to FIGS. 2A and 2B, in some patients, the glenoid 28 of a patient's scapula 30 may be severely eroded to an extent that a metaglene component 60 cannot be properly implanted. In such situations, surgeons may attach the metaglene component 60 to a bone graft that fills in the eroded space in the glenoid. The bone graft 90 can be resected from an allograft or a part of the patient's body, such as the head of the humerus or portion of the femur. For example, the bone graft 90 can be cylindrically-shaped and have a generally concave proximal surface 92 in which a bore is drilled at least partially through the graft to receive the post 64 of the metaglene component 60.

Figure 7A:
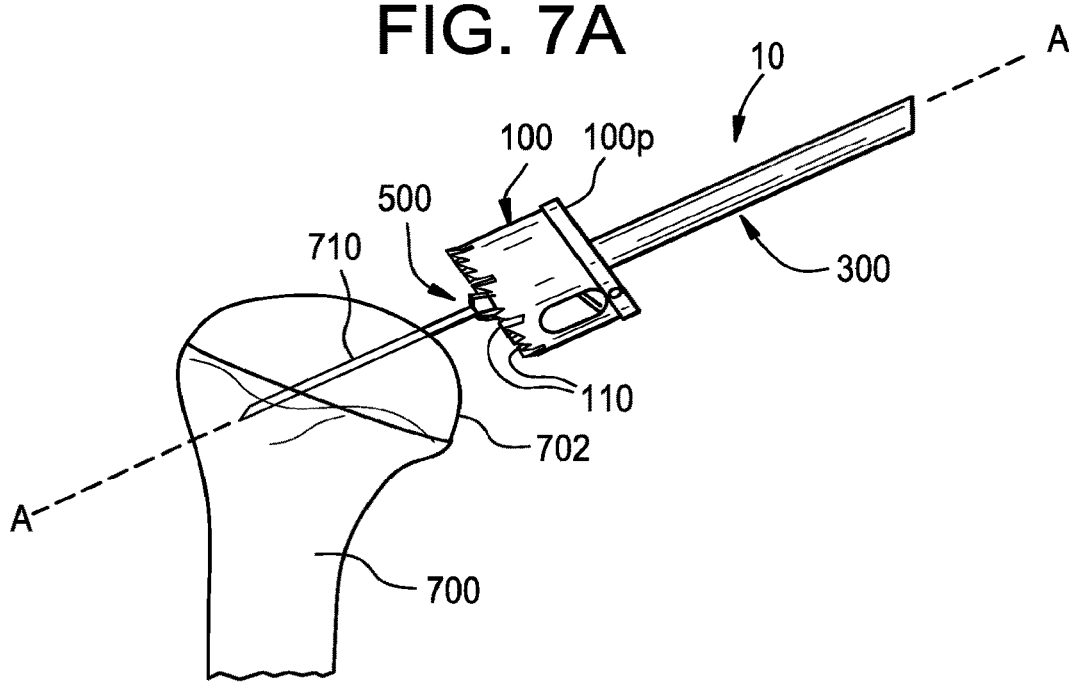
FIGS. 7A-7F are schematic illustrations of one exemplary embodiment of a method of resecting a bone graft using an annular cutting tool, like the tool of FIG. 1A.

FIGS. 7A-7F are schematic illustrations of one exemplary embodiment of a method of resecting a bone graft using an annular cutting tool, like the tool of FIG. 1A. As shown in FIG. 7A, a guide pin 710 can be drilled through an approximate center or other location of a head 702 of a humerus 700. The annular cutting tool 10, or reamer, can be attached to a power drill or other rotary power tool (not shown). For example, the shank 320 at the proximal end 300p of the drive shaft 300 can be attached to a chuck of a power drill (or other coupling mechanism of a rotary power tool). The reamer 10 can be positioned relative to the humeral head 702 by inserting the cannulated drill bit 500 over the guide pin 710 that protrudes, or otherwise extends, from the head. The operator can distally advance the power drill coupled to the reamer 10 over the guide pin 710 until the distal cutting tip 520 of the drill bit 500 and/or the cutting teeth 110 of the annular cutting body 100, whichever is more or equally distal to the other, abuts the boney surface of the humeral head 702.

Figure 7B:
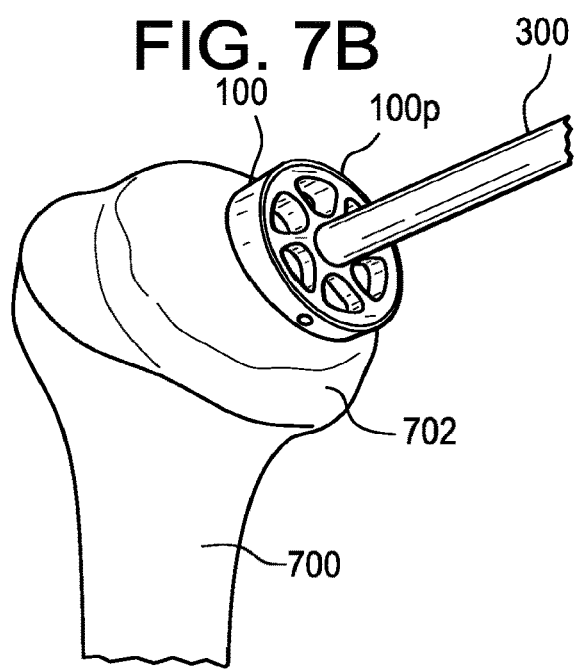

When the operator actuates the power drill, the drive shaft 300 transfers the torque applied by the power drill to the annular cutting body 100 and the cannulated drill bit 500 such that the reamer 10 spins about a longitudinal axis A-A. As shown in FIG. 7B, the operator distally advances the power drill while the reamer 10 is spinning such that the teeth 110 of the annular cutting body 100 make a circular cut into the bone of the humeral head 702. As the annular cutting body 100 cuts into the bone, the cannulated drill bit 500 drills a central hole into the bone within the diameter of the circular cut. When the proximal end 100p of the annular cutting body 100 reaches the surface of the humeral head 702, the surface reaming blades 200 can ream the proximal end of the bone to have a concave, convex, or other shaped surface.

Notably, as the power drill, and thus the reamer 10, is being distally advanced into the humeral head 702, and the reamer 10 is being spun, only the cutting teeth 110 are in contact with the bone. This is due, at least in part, to the flared configuration of the teeth 110 described above, juxtaposed against the recessed surface area 102 of the annular cutting body 100. As a result, while distally advancing the power drill and reamer 10 during cutting, a portion of the annular cutting body 100 that is directly proximal to the plurality of cutting teeth 110 does not contact the bone from which a bone graft is being removed. The "does not contact" aspect is referencing bone that is part of the bone being cut, i.e., bone that has not yet been cut, recognizing that bone debris from cut bone may contact any portion of the reamer 10, and in fact portions of the reamer 10 are designed to receive such debris and/or allow such debris to pass therethrough. The portion of the annular cutting body 100 that is directly proximal to the plurality of cutting teeth 110 that does not contact the bone from which a bone graft is being removed can be, for example, a portion of the annular cutting body 100 that extends around an entire circumference of the body 100, up to and including the entire recessed surface 102. In other embodiments, a smaller section of the central portion of the body 100 does not contact bone during the cutting process. A significant distinction of the present configuration is that the amount of the tool 10 that contacts the bone is reduced due to the configuration and location of the teeth 110 with respect to other portions of the annular cutting body 100.

Figure 7C:
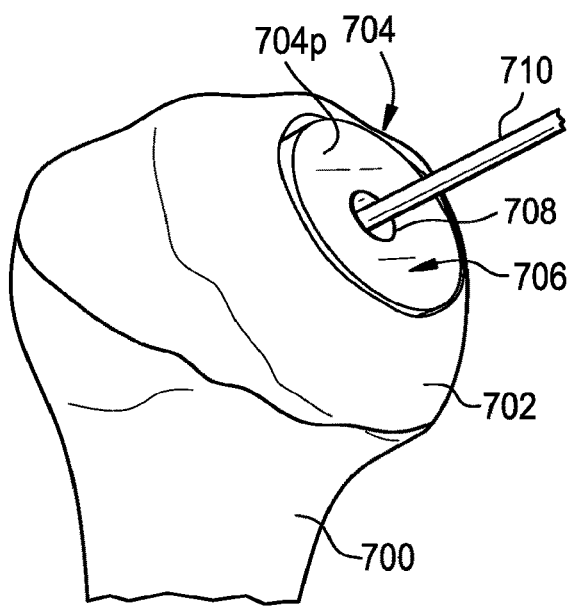

The reamer 10 can be removed from the surgical site when the cutting, drilling, and reaming of the humeral head 702 is complete, thereby exposing an annular shaped bone graft. For example, as shown in FIG. 7C, the annular shaped bone graft 704 can have a cylindrically-shaped body 706 cut by the spinning annular cutting body 100 and a central hole 708 drilled by the spinning drill bit 500. The proximal surface 704p of the bone graft 704 can have a concave surface formed by the spinning surface reaming blades 200. The guide pin 710 can remain in place when the reamer 10 is removed.

Figure 7D:
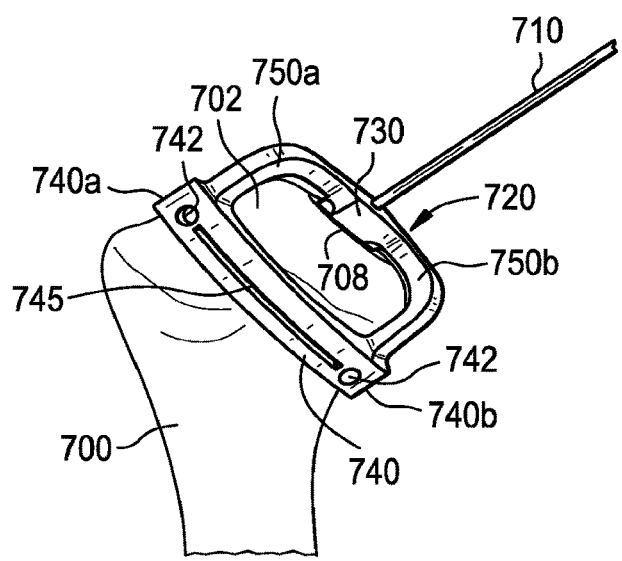

As shown in FIG. 7D, after the reamer 10 is removed, a resection guide 720 can be attached to the humeral head 702 for aligning an oscillating saw or other linear cutting tool. The saw or other cutting tool can be operated to resect the annular shaped bone graft 704 from the bone. In the illustrated embodiment, the resection guide 720 includes a central alignment plug 730, an arcuate guide bar 740, and a pair of extension arms 750a and 750b (collectively 750) that fixedly couple the alignment plug to the guide bar. The resection guide 720 can be attached to the humeral head 702 by inserting the alignment plug 730 into the central hole 708 of the bone graft 704. Each of the extension arms 750 can have a substantially L-shaped body that is configured to extend laterally from the central plug 730 and distally to a respective end 740a, 740b of the arcuate guide bar 740. The distal ends of the extension arms 750 can be configured to position the arcuate guide bar 740 substantially perpendicular to a longitudinal axis of the guide pin 710 at a desired depth relative to the proximal end of the bone graft 704.

Figure 7E:
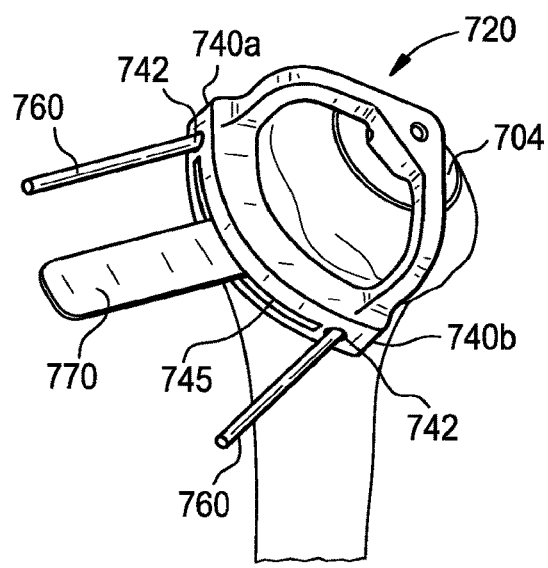
Figure 7F:
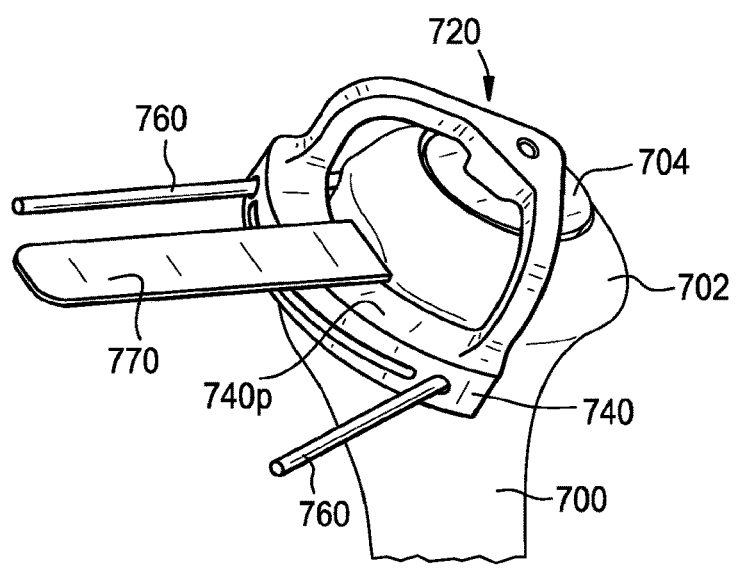

As shown in FIG. 7E, stabilization pins 760 can be inserted through peripheral holes 742 defined at the respective ends 740a and 740b of the arcuate guide bar 740 to fix the resection guide 720 in place. Once the resection guide 720 is fixed, the guide pin 710 can be removed and an oscillating saw 770, or other linear cutting tool, can be advanced along the slot 745 of the arcuate guide bar 740 to make a lateral cut through the humeral head 702, thereby resecting the annular shaped bone graft 704. Alternatively, as shown in the illustrated embodiment of FIG. 7F, the operator can advance the oscillating saw 770 along the proximal surface 740p of the arcuate guide bar 740 as a guide to make a lateral cut through the humeral head 702, resulting in the height of the resected bone graft 704 being shorter than the bone graft resected using the slot 745 of the accurate guide bar 740. In some embodiments, the resected bone graft 104 can have a height approximately in the range between about 5 mm and approximately 30 mm. For example, the resected bone graft 104 can have a height that is about 10 mm or that is about 15 mm.

While the annular cutting tools and methods illustrated and described herein generally involve resecting bone grafts for use in total or reverse shoulder replacement procedures, it will be appreciated that the annular cutting tools and methods herein can be used with various other types of surgical procedures that may involve resecting bone grafts.

A person skilled in the art, in view of the present disclosures, will also understand how the disclosures provided for herein can be adapted to resect cylindrically-shaped grafts and/or plugs in any bone, non-bone, or non-living objects or substrates without departing from the spirit of the present disclosure. Likewise, a person skilled in the art, in view of the present disclosures, will understand how the disclosures provided for herein can be adapted for other cutting purposes outside of the surgical or medical field. For example, annular cutting tools or coring tools used in other industries can be modified or adapted to include cutting teeth according to the present disclosures for metal cutting, wood cutting, and/or cutting or reaming any material that is softer than the cutting tool itself.

The annular cutting tools disclosed herein, and the various component parts thereof, can be constructed from any of a variety of known materials. Exemplary materials include those that are suitable for use in surgical applications, including, without limitation, metals (e.g., stainless steel, titanium, aluminum, or alloys thereof), ceramics, and materials that can be hard coated with wear and abrasion resistant coatings. Exemplary materials can also include 3D-printed powders and alloys of 3D printing binder jet materials, metal-injection-molded materials, which can include alloy steels, tungsten-carbide materials or like hard materials, and ceramics. Exemplary materials can also include polymers or polymer reinforced composites. The various components of the devices disclosed herein are typically rigid.

The devices disclosed herein can be designed to be disposed of after a single use, or they can be designed to be used multiple times. In either case, however, the device can be reconditioned for reuse after at least one use. In particular, in instances in which the device is not a unitary component, reconditioning can include any combination of the steps of disassembly of the device, followed by cleaning or replacement of particular pieces, and subsequent reassembly. Any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

Preferably, the devices described herein will be processed before surgery. First, a new or used instrument is obtained and if necessary cleaned. The instrument can then be sterilized. In one sterilization technique, the instrument is placed in a closed and sealed container, such as a plastic or TYVEK® bag. The container and its contents are then placed in a field of radiation that can penetrate the container, such as gamma radiation, x-rays, or high-energy electrons. The radiation kills bacteria on the instrument and in the container. The sterilized instrument can then be stored in the sterile container. The sealed container keeps the instrument sterile until it is opened in the medical facility.

It is preferred that device is sterilized. This can be done by any number of ways known to those skilled in the art including beta or gamma radiation, ethylene oxide, steam.

The preceding description of the disclosed embodiments is provided to enable any person skilled in the art to make or use the claims. Various modifications to these embodiments will be readily apparent to those skilled in the art, and the generic principles defined herein may be applied to other embodiments without departing from the scope of the claims. Thus, the present disclosure is not intended to be limited to the embodiments shown herein but is to be accorded the widest scope consistent with the following claims and the principles and novel features disclosed herein. All publications and references cited herein are expressly incorporated herein by reference in their entirety.

The invention claimed is:

1. A method of resecting a bone graft, comprising:
positioning an annular cutting tool with respect to a bone, the annular cutting tool having a drill bit and an annular cutting body disposed circumferentially around at least a portion of the drill bit, the annular cutting body having a plurality of cutting teeth disposed at a distal end thereof, the plurality of cutting teeth extending radially outward beyond a central portion of the annular cutting body with respect to a central longitudinal axis of the cutting tool, and the annular cutting body also having an annular protrusion disposed at a proximal end thereof, the annular protrusion extending radially outward beyond the central portion of the annular cutting body with respect to the central longitudinal axis of the cutting tool, the central portion of the annular cutting body comprising a recessed surface area that is bound by the plurality of cutting teeth and the annular protrusion, and the annular protrusion being monolithic with respect to the recessed surface area of the annular cutting body;
applying a torque to the annular cutting tool to cause the plurality of cutting teeth to rotate about a longitudinal axis of the cutting tool; and
distally advancing the annular cutting tool into the bone while the torque is being applied to cause the plurality of cutting teeth to contact and cut the bone, thereby defining a bone graft, while the recessed surface area does not contact the bone from which the bone graft is being removed and bone debris from the bone collects on the recessed surface area of the annular cutting body, the distal advancement also causing the drill bit to ream a hole in the defined bone graft.

2. The method of claim 1, wherein the drill bit is cannulated and positioning the annular cutting body comprises distally inserting the cannulated drill bit over a guide pin extending from the bone.

3. The method of claim 1, wherein one or more teeth of the plurality of cutting teeth has a flat distal tip.

4. The method of claim 3, wherein a longitudinal plane defined by a distal face of the flat distal tip is perpendicular to the central longitudinal axis.

5. The method of claim 1, wherein distally advancing the annular cutting tool into the bone while the torque is being applied further causes one or more blades of the annular cutting tool disposed proximal of the plurality of cutting teeth to shape a proximal surface of the bone graft.

6. The method of claim 5, wherein the one or more blades extend radially outward from the central longitudinal axis in a spiral pattern.

7. The method of claim 5, wherein the annular body is coupled to the drill bit by a plurality of support arms extending radially outward from a distal end of the drill bit to an outer perimeter of the annular cutting body.

8. The method of claim 7, wherein the one or more blades are defined on a distal-facing surface of the plurality of support arms.

9. The method of claim 1, wherein distally advancing the annular cutting tool results in formation of the bone graft in a single distal advancement of the annular cutting tool, without having to pull back the annular cutting tool.

10. The method of claim 1, wherein while distally advancing the annular cutting tool into the bone while the torque is being applied is such that the central portion does not contact the bone.

11. The method of claim 1,
wherein distally advancing the annular cutting tool into the bone while the torque is being applied further causes bone debris to pass through a plurality of gullets formed through the annular cutting body, each gullet of the plurality of gullets being disposed between adjacent teeth of the plurality of cutting teeth, and
wherein one or more of the plurality of gullets is an extended gullet, each extended gullet having more than one tooth of the plurality of cutting teeth disposed between an adjacent extended gullet.

12. The method of claim 1,
wherein the drill bit terminates at a flared distal cutting tip, and
wherein distally advancing the annular cutting tool into the bone while the torque is being applied further causes bone debris to be diverted proximally from the bone along two or more twisted grooves extending longitudinally on the drill bit.

13. A method of resecting a bone graft, comprising:
positioning an annular cutting tool with respect to a bone, the annular cutting tool having a drill bit and an annular cutting body disposed circumferentially around at least a portion of the drill bit, the annular cutting body having a plurality of cutting teeth disposed at a distal end thereof;
applying a torque to the annular cutting tool to cause the plurality of cutting teeth to rotate about a longitudinal axis of the cutting tool; and
distally advancing the annular cutting tool into the bone while the torque is being applied to cause the plurality of cutting teeth to contact and cut the bone, thereby defining a bone graft, while a portion of the annular cutting body directly proximal to the plurality of cutting teeth does not contact the bone from which the bone graft is being removed, and to cause the drill bit to ream a hole in the defined bone graft;
wherein one or more blades of the annular cutting tool disposed proximal of the plurality of cutting teeth divert debris from an interior of the annular cutting body through one or more openings defined by the blades.

14. The method of claim 13, wherein the drill bit is cannulated and positioning the annular cutting body comprises distally inserting the cannulated drill bit over a guide pin extending from the bone.

15. The method of claim 13, wherein one or more teeth of the plurality of cutting teeth has a flat distal tip.

16. The method of claim 15, wherein a longitudinal plane defined by a distal face of the flat distal tip is perpendicular to the longitudinal axis.

17. The method of claim 13, wherein distally advancing the annular cutting tool results in formation of the bone graft in a single distal advancement of the annular cutting tool, without having to pull back the annular cutting tool.

18. The method of claim 13,
wherein the drill bit terminates at a flared distal cutting tip, and
wherein distally advancing the annular cutting tool into the bone while the torque is being applied further causes bone debris to be diverted proximally from the bone along two or more twisted grooves extending longitudinally on the drill bit.

19. The method of claim 13, wherein the one or more blades extend radially outward from the longitudinal axis in a spiral pattern.

20. The method of claim 13, wherein the annular body is coupled to the drill bit by a plurality of support arms extending radially outward from a distal end of the drill bit to an outer perimeter of the annular cutting body.

\* \* \* \* \*